Figure 1:
Figure 1:
Figure 1:
Figure 1:
Figure 1:

US005698430A

United States Patent [19]

Rubinstein et al.

[11] Patent Number: 5,698,430
[45] Date of Patent: Dec. 16, 1997

[54] NON-INFECTIVE VACCINES

[76] Inventors: Alan I. Rubinstein, 10600 Wilshire Blvd., Los Angeles, Calif. 90024; Daniel B. Rubinstein, 40 Eliot Crescent, Brookline, Mass. 02167

[21] Appl. No.: 339,343

[22] Filed: Nov. 14, 1994

Related U.S. Application Data

[63] Continuation-in-part of Ser. No. 004,931, Jan. 15, 1993, abandoned.

[51] Int. Cl.$^6$ .............................. C12N 7/04; C12N 7/06; C12N 7/02; A61K 39/21
[52] U.S. Cl. .................... 435/236; 435/238; 435/239; 435/270; 424/208
[58] Field of Search ................ 424/208.1; 435/236, 435/238, 239, 270

[56] References Cited

U.S. PATENT DOCUMENTS

| | | | |
|---|---|---|---|
| 5,106,619 | 4/1992 | Wiesehahn | 424/89 |
| 5,168,053 | 12/1992 | Altman et al. | 435/91 |
| 5,242,820 | 9/1993 | Lo | 435/240.2 |

OTHER PUBLICATIONS

Charoenvit, et al. 1991, "Inability of malaria vaccine to induce . . . ," Science 251: 668–671.
Hoffman, et al, 1987, "Naturally acquired anhbodies to sporozoiles . . . " Science 231: 639–642.
Skelly, et al, 1981, "Formaldehyde treatment of hepatitis . . . " J. Virol. Methods 3: 51–59.
Fox, 1994, "No Winners against AIDS". Biotechnology 12: 128.

*Primary Examiner*—Lynette F. Smith
*Attorney, Agent, or Firm*—Ostrolenk, Faber, Gerb & Soffen, LLP

[57] ABSTRACT

A method of producing a vaccine comprising providing a quantity of the disease-causing entity, treating the quantity to remove or disrupt a majority of the nucleic acid present in the quantity sufficient to render the quantity non-infective while maintaining the structure of the proteins and glycoproteins on the surface of the entity to render the vaccine protective. A method of producing a vaccine to human pathogenic retroviruses comprising the steps of partially solubilizing a quantity of the virus to produce a suspension, adding a proteinase to the suspension to release viral nucleic acids from the viral coat proteins, treating the suspension to disrupt or remove sufficient viral nucleic acids to render the suspension substantially or completely non-infective and verifying the sufficient disruption or removal of viral nucleic acids from the suspension.

10 Claims, 1 Drawing Sheet

VIRUS PARTICLES

| PARTIAL SOLUBILIZATION OF VIRUS PARTICLES |

| NUCLEIC ACID INACTIVATION |

| VERIFICATION OF NUCLEIC ACID INACTIVATION |

| CONCENTRATION OF VIRAL PROTEINS |

VACCINE

NON-INFECTIVE VACCINES

CROSS-REFERENCE TO RELATED APPLICATION

The present Application is a Continuation-in-Part of our Application 08/004,931 filed Jan. 15, 1993 now abandoned, entitled "NOVEL NON-INFECTIVE VACCINES", the contents of which are incorporated herein by reference in their entirety.

BACKGROUND

Viruses cause a myriad of diseases in humans and animals. Approaches to the control of virus-caused human disease include vaccination, antiviral therapy and public health measures. Of these approaches, vaccination is the least costly and most effective way of controlling virus-caused diseases.

The production of suitable vaccines, however, present a number of challenges. First, vaccines derived from whole-killed or whole-attenuated viruses, may retain residual disease-causing activity. Secondly, vaccines must elicit immune responses to a sufficient number of viral antigens to confer immunity against a viral challenge. Therefore, an ideal vaccine would retain enough specific viral antigens to confer immunity while reducing or eliminating the risk of causing disease through the vaccine.

Present attempts to produce a safe vaccine consist of selective removal of genes. However, these attempts leave substantial numbers of genes increasing the risk of viable infective entities in the vaccine.

Therefore, many virus-caused diseases do not yet have satisfactory vaccines available because experimental vaccines either are not sufficiently immunogenic or because the vaccines are associated with a significant risk of disease caused by the vaccine or both. Thus, there is a need for vaccines against many virus-caused and non-virus caused diseases that are sufficiently immunogenic while carrying no risk or insignificant risk of causing disease.

SUMMARY

The present invention is directed to vaccines that satisfies these needs. A method of producing a vaccine to a virus-caused or non-virus caused disease having features of the present invention comprises partially solubilizing a quantity of the virus, or other organism, in a proteinase buffer to produce a suspension. A proteinase is added to the suspension and the suspension incubated to release viral nucleic acids from the viral coat proteins and glycoproteins. Next, the suspension is treated to disrupt or remove sufficient viral nucleic acids to render the suspension substantially or completely non-infective. This treatment can be accomplished by using a nuclease, with or without subsequent formaldehyde treatment. The sufficient disruption or removal of viral nucleic acids from the suspension is then verified. The verification can be accomplished through either Northern or Southern blots with residual nucleic acids amplified by the polymerase chain reaction (PCR). Finally, the viral coat proteins are concentrated and additional materials added as needed for the vaccine. This method is suitable for producing a vaccine against HIV-1 and HIV-2, and other viruses, as well as other microorganisms such as bacteria and protozoa.

A method of producing a vaccine having features of the present invention comprises the steps of providing a quantity of the disease-causing entity. The quantity is treated to remove or disrupt sufficient nucleic acid to abolish infectivity while retaining sufficient antigenicity of surface proteins, glycoproteins and epitopes of the disease-causing entity to render the vaccine protective. The method is suitable to produce a vaccine for diseases caused by bacteria, protozoa or viruses. The treating step may be accomplished by exposing a quantity of the disease-causing entity to a nuclease such as deoxyribonuclease, ribonuclease or both.

A vaccine for conferring immunity against a virus-caused disease having features of the present invention comprises a quantity of virus wherein a majority of nucleic acid has been removed or disrupted while substantially preserving all coat proteins and glycoproteins and epitopes to retain their antigenicity. The vaccine can further comprise a pharmaceutically acceptable carrier or an adjuvant. In one version of the present invention, at least sixty percent of the nucleic acid has been removed or disrupted. In another version, substantially all the nucleic acid has been removed or disrupted.

A method of immunizing an animal against a virus-caused or non-virus caused disease having features of the present invention comprises the steps of providing a quantity of virus, removing or disrupting a majority of nucleic acid while leaving sufficient immunogenic coat protein and glycoprotein to elicit a protective immune response, and immunizing the animal by an acceptable route to produce immunity.

FIGURE

These and other features, aspects, and advantages of the present invention will become better understood with regard to the following description, appended claims, and accompanying Figure where:

FIG. 1 is a flowchart showing the steps of producing a vaccine according to one version of the present invention.

DESCRIPTION

According to one version of the present invention, there is provided a method of making a vaccine for conferring immunity against a virus-caused disease. The vaccine is derived from whole virus particles which are treated to remove or disrupt the majority of nucleic acids present in the virus particles under conditions which retain the antigenic activity of substantially all of the viral coat proteins or glycoproteins. By so treating the virus particles, it is possible to reduce or eliminate the possibility that the vaccine will itself transmit the disease while producing a vaccine that confers immunity against the virus-caused disease.

The method of vaccine production according to one version of the present invention results in a maximum possible number of antigenic regions of viral coat proteins and glycoproteins by preparing the vaccine from whole viruses. This is in contrast to synthetically prepared immunogens and recombinants which include more limited numbers of antigenic sites.

This method for vaccine production is appropriate for a wide variety of virus-caused diseases, as well as diseases caused by non-viruses such as bacteria and protozoa. Viral diseases suitable for vaccine production by this method include those diseases caused by viruses of the families Retroviridea, Picornaviridae, Flaviviridea, Rhabdoviridea, Hepadnaviridae, Adenoviridae, Poxviridae, Orthomyxoviridae and Paramyxoviridae. Examples of such diseases include polio, measles, mumps, rabies, rubella, yellow fever, vaccinia, influenza, rabies, viral-induced leukemia, viral-induced lymphoma, AIDS, Hepatitis A, Hepatitis B and Hepatitis C.

In one preferred version of the present invention, there is provided a vaccine conferring immunity against one or more of the human diseases caused by retroviruses. These retroviruses include HIV-1 and HIV-2 which cause AIDS, and HTLV-I and HTLV-II, which cause viral-induced leukemia and lymphoma. HIV-1 proteins and glycoproteins which may function as antigens include transmembrane gp41 (env), core p18 (gag), core p24 (gag), gp160, p65, p55, p40, p31. HIV-2 proteins and glycoproteins which may function as antigens include outer envelope gp125 (env), transmembrane gp36 (env), core p16 (gag), core p26 (gag), gp140, p68, p56 and p55. A vaccine against HIV-caused diseases, according to one version of the present invention prepared from whole viruses, contains all of these proteins and glycoproteins which may function as antigens as well as other proteins or glycoproteins present in HIV, including gp120. Therefore, the vaccine improves neutralization of the virus by eliciting an antibody response to this important glycoprotein.

According to one version of the present invention, a vaccine for conferring immunity against a virus-caused disease is prepared from a quantity of the virus by removing or disrupting a majority of the nucleic acid present in the virus. It is understood that residual amounts of DNA or RNA may remain which are inconsequential with respect to infectivity of the vaccine. In a preferred version, at least 60% of the nucleic acid is removed. In another particularly preferred version, substantially all of the nucleic acid is removed. For vaccines directed against retrovirus-caused disease such as AIDS, in addition to removing the majority of nucleic acid present in the viruses, viral reverse transcriptase is also preferentially removed. After removal of nucleic acid, and reverse transcriptase, the remaining envelope protein and glycoproteins are substantially intact such that they retain sufficient antigenicity to confer protection. A pharmaceutically acceptable carrier, an adjuvant or both can be added as desired.

According to another version of the present invention, there is provided a method of producing a vaccine to protect against a virus-caused disease in a human. First, a quantity of the virus is obtained. Next, the quantity of the virus is treated to remove or disrupt a majority of viral nucleic acid present in the quantity of virus. This treatment can consist of exposing the virus to a nuclease, such as ribonuclease or deoxyribonuclease or both ribonuclease and deoxyribonuclease. The treatment can further comprise exposing the quantity of virus to formaldehyde. In a preferred version, at least 60% of the nucleic acid is disrupted or removed during treatment. In a particularly preferred version, substantially all the nucleic acid is disrupted or removed. The sufficient lack of nucleic acid can be confirmed in the quantity by a Northern blot (for RNA), a Southern blot (for DNA) and of residual nucleic acid amplified by the polymerase chain reaction (PCR) as is understood by those with skill in the art.

One advantage of the method of producing a vaccine according to the present invention is that it can be used in the cases of rapidly mutating viruses such as human retroviruses which cause AIDS. As new antigen variants emerge, the method of vaccine production can be reperformed removing the nucleic acid of the mutate strains and a new vaccine produced. For instance, a combined vaccine against HIV-1 and HIV-2 can be produced by the method disclosed herein. As new subtypes HIV emerge, a vaccine for these additional subtypes can be produced by using the subtypes as part of the starting material, thus incorporating the subtypes into the vaccine.

According to another version of the present invention, there is provided a method of immunizing an animal against a virus-caused disease. The virus-caused disease can be AIDS, another disease caused by a retrovirus, or another virus or another disease.

The method of immunizing an animal comprises first providing a quantity of the virus known to cause the disease. Next, a majority of nucleic acid present in the quantity of virus is removed or disrupted such as by the treatment with a nuclease, with or without additional treatment by formaldehyde. This treatment is performed in a manner which leaves sufficient protein or glycoprotein present to elicit a protective immune response. The resultant composition can be combined with a pharmaceutically acceptable carrier with or without an adjuvant if desired as is understood by those with skill in the art. Finally, the composition is administered to the animal to be protected by an acceptable route, thereby producing immunity against a virus-caused disease.

Besides being used to prepare vaccines, the method according to the present invention can be used for other purposes. For example, a quantity of virus or other organisms can have the viral coat proteins or other organism proteins concentrated by the method, thereby reducing or eliminating the potential infectivity of the quantity, and the concentrated proteins used for determination of protein composition or protein properties.

A vaccine according to one version of the present invention is prepared as follows. First, a quantity of whole virus is partially solubilized, that is solubilized under sub-optimal conditions to preserve the antigenicity of viral coat proteins and glycoproteins. Second, viral nucleic acids liberated in the first step are disrupted or removed, such as by hydrolysis with nucleases or with basic solutions. Third, disruption or removal of viral nucleic acids is confirmed by Northern blot analysis for RNA or Southern blot analysis for DNA, followed by or in the alternate by PCR amplification using preselected viral gene sequences as PCR primers. An example of vaccine preparation according to one version of the present invention is described in greater detail below.

EXAMPLE 1

(PROSPECTIVE)

PREPARATION OF A NON-INFECTIVE VACCINE

Referring now to FIG. 1, there is illustrated a flowchart showing the steps of producing a vaccine according to one version of the present invention. The method can be used for viruses and non-viruses, such as bacteria or protozoa, including Plasmodium falciparum the causative agent of malaria.

(a) Partial Solubilization of Virus Particles

A suspension is made from a titered quantity of virus which is added to 100 ml of proteinase digestion buffer comprising 20 mM Tris-Cl (pH 7.4), 20 mM EDTA (pH 8) and 0.5% sodium dodecyl sulfate. Next, proteinase K is added to the suspension to produce a concentration of 100 mg/ml. The suspension is incubated, thereby, partially solubilizing the viral particles. The incubation is carried up to, but not beyond a point at which viral proteins remain intact and retain sufficient tertiary structure in antigen sites to bind known monoclonal antiviral protein coat antibodies (e.g., anti-gp41 and anti-gp120 in the case of HIV) on ELISA. The intactness of the viral proteins and retention of sufficient tertiary structure is demonstrated by standard Western blot.

(b) inactivation of Nucleic Acids by Disruption or Removal

Next, viral nucleic acids liberated in step (a) are inactivated by disruption or removal from the suspension. For virus particles containing RNA, this step is accomplished by treating the suspension with heat pre-activated RNase at 37° C for at least about one hour. For virus particles containing DNA, this step is similarly accomplished by treating the suspension with a great excess of DNase. For virus particles containing RNA, the RNase treatment can be substituted with, or followed sequentially by, making the suspension sufficiently basic (pH >10) to assure RNA hydrolysis.

(c) Verification of Nucleic Acid Inactivation

Next, sufficient disruption or removal for inactivation of viral nucleic acid from the suspension is verified. For viral RNA this is accomplished by size fractionation on Northern gels, followed by blotting onto nylon membranes and hybridization to radiolabeled complementary viral sequences. Sufficient disruption or removal for inactivation of viral DNA is verified by size fractionation on Southern blots and hybridization to complementary gene probes. Absence of hybridization in either case verifies sufficient disruption or removal of nucleic acids.

Alternately or sequentially, sufficient disruption or removal of viral nucleic acid is verified by PCR, which greatly increases the sensitivity of detection of any residual nucleic acids. PCR is performed using primers derived from the 5' and 3' ends of all known genes specific to the virus in the amplification process and using samples of the suspension as templates. The amplification products are then analyzed using Northern gels (for RNA) and Southern gels (for DNA), and radiolabeled complementary sequences. The lack of amplification products on these gels verifies sufficient disruption or removal of nucleic acids.

(d) Concentration of Viral Proteins

Then, viral coat proteins remaining in the suspension are then collected and concentrated. Collection is accomplished by ammonium sulfate precipitation and concentration to a desired level according to methods known to those with skill in the art. This concentrated suspension contains molecules in a wide range of molecular weights from short polypeptides to substantially intact proteins, allowing for exposure of the greatest range of antigen sites and maximal antigenicity of the material. A pharmaceutically acceptable carrier or an adjuvant is added if desired.

Although the present invention has been described in considerable detail with reference to certain preferred versions thereof, other versions are possible. For example, the method of producing non-infective viral vaccines can be used to produce vaccines for diseases caused by non-viral organisms such as bacteria, e.g Hemophilus influenzae, and protozoa, e.g. Plasmodium falciparum, the causative agent of malaria. Therefore, the spirit and scope of the appended claims should not be limited to the description of the preferred versions herein.

We claim:

1. A method of reducing or eliminating the infectivity of a quantity of virus by removing viral nucleic acid from the quantity while leaving viral coat proteins consisting of the following steps in order:
   (i) partially solubilizing the quantity of the virus in a proteinase digestion buffer to produce a suspension, the virus having viral nucleic acids in viral coat proteins;
   (ii) adding a proteinase to the suspension and incubating the suspension to release the viral nucleic acids from the viral coat proteins and glycoproteins;
   (iii) treating the suspension to disrupt or remove sufficient viral nucleic acids to render the suspension with a nuclease at least substantially non-infective;
   (iv) verifying that the suspension is non-infective; and
   (v) collecting and concentrating the viral coat proteins in the treated and verified suspension.

2. The method of claim 1, wherein the virus is a HIV-1 or HIV-2.

3. A method of producing a composition consisting of a disease-causing microorganism, selected from the group consisting of viruses, bacteria and protozoa, by treating said microorganism, with a nuclease to remove or disrupt nucleic acid present while retaining antigenicity of surface proteins and glycoproteins of the disease-causing microorganism.

4. The method of claim 3, wherein the treating step consists of exposing the quantity of disease causing entity to a nuclease selected from the group consisting of deoxyribonuclease, ribonuclease and both of the foregoing.

5. The method of claim 3, further consisting of a step of exposing the quantity of disease causing entity to formaldehyde after the treating step.

6. The method of claim 3, further consisting of a step of combining the quantity of disease causing entity with an adjuvant after the treating step.

7. The method of claim 3, wherein the treating step consisting of removing or disrupting at least about 60% of the nucleic acid present in the quantity of disease causing entity.

8. The method of claim 3, wherein the treating step consists of removing or disrupting substantially all of the nucleic acid present in the quantity of disease causing entity.

9. The method of claim 3, further consisting of a step of verifying disruption or removal of nucleic acid in the quantity by PCR after the treating step.

10. The method of claim 3, further consisting of a step of verifying disruption or removal of nucleic acid in the quantity by performing a Northern blot or a Southern blot after the treating step.

* * * * *